US008298201B2

(12) United States Patent
Albrectsen

(10) Patent No.: US 8,298,201 B2
(45) Date of Patent: Oct. 30, 2012

(54) CLEANABLE FILTER FOR AN OSTOMY APPLIANCE

(75) Inventor: Lasse Skoett Albrectsen, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 1095 days.

(21) Appl. No.: 11/666,914

(22) PCT Filed: Nov. 3, 2005

(86) PCT No.: PCT/DK2005/000703
§ 371 (c)(1),
(2), (4) Date: Jul. 31, 2008

(87) PCT Pub. No.: WO2006/048019
PCT Pub. Date: May 11, 2006

(65) Prior Publication Data
US 2008/0306459 A1    Dec. 11, 2008

(30) Foreign Application Priority Data
Nov. 3, 2004   (DK) ................................. 2004 01689

(51) Int. Cl.
*A61F 5/44* (2006.01)
(52) U.S. Cl. ........ 604/333; 604/332; 604/334; 604/335; 604/336; 604/337; 604/338; 604/339; 604/340; 604/341; 604/342; 604/343; 604/344; 604/345; 604/346; 604/347; 604/348; 604/349; 604/350; 604/351
(58) Field of Classification Search ................... 604/332, 604/333, 334–351
See application file for complete search history.

(56) References Cited

U.S. PATENT DOCUMENTS

| 4,039,448 | A | * | 8/1977 | Etani ............................. 210/702 |
| 4,211,224 | A | * | 7/1980 | Kubach et al. ................ 604/333 |
| 4,303,533 | A | * | 12/1981 | Fremont ....................... 210/791 |
| 4,367,742 | A | | 1/1983 | Ornstein |
| 4,460,392 | A | * | 7/1984 | Poulsen et al. .................. 96/134 |
| 4,490,145 | A | | 12/1984 | Campbell |
| 4,668,258 | A | | 5/1987 | Steer |
| 4,723,951 | A | | 2/1988 | Steer |

(Continued)

FOREIGN PATENT DOCUMENTS

CN    1 251 980    5/2000

(Continued)

*Primary Examiner* — Tatyana Zalukaeva
*Assistant Examiner* — Ginger T Chapman
(74) *Attorney, Agent, or Firm* — Coloplast Corp., Coloplast A/S; Daniel G. Chapik; Nicholas R. Baumann

(57) ABSTRACT

The present invention relates to an in situ cleanable filter for an ostomy appliance comprising a pathway for leading gases to a vent in an ostomy bag and a protective element contained in said pathway to prevent solid or semi-liquid waste from blocking the pathway where a channel or compartment formed by liquid impermeable layer(s) is defining at least part of the pathway and at least a part of said compartment or channel contain a protective element of an open celled compressible material having a memory and having a pore size of at least 60 PPI, said protective element extending in the same direction as the gas flow within the channel or compartment, said channel or compartment having an opening providing access to the pathway from the interior of the bag, said pathway having another opening being connected to a vent in the ostomy bag, optionally via a deodorizing filter.

The invention relates to an ostomy appliance comprising a filter as above and a method for emptying and cleaning the filter.

23 Claims, 9 Drawing Sheets

U.S. PATENT DOCUMENTS

| | | | |
|---|---|---|---|
| 5,167,650 A * | 12/1992 | Johnsen et al. | 604/332 |
| 5,306,264 A * | 4/1994 | Ferguson et al. | 604/333 |
| 5,417,678 A | 5/1995 | Baumann et al. | |
| 5,643,234 A * | 7/1997 | Lesko | 604/333 |
| 5,733,271 A * | 3/1998 | Bjørn | 604/333 |
| 6,135,976 A | 10/2000 | Tachibana et al. | |
| 6,135,986 A | 10/2000 | Leisner et al. | |
| 6,214,095 B1 * | 4/2001 | Logan et al. | 96/147 |
| 6,659,988 B1 * | 12/2003 | Steer et al. | 604/333 |
| 2003/0140794 A1 * | 7/2003 | Wang et al. | 96/226 |
| 2007/0282284 A1 * | 12/2007 | Mullejans et al. | 604/333 |

FOREIGN PATENT DOCUMENTS

| | | |
|---|---|---|
| EP | 0 191 646 A2 | 8/1986 |
| EP | 0 607 028 A1 | 7/1994 |
| GB | 2276324 A * | 9/1994 |
| JP | 6277245 | 10/1994 |
| WO | WO 98/44880 | 10/1998 |

* cited by examiner

AA

CLEANABLE FILTER FOR AN OSTOMY APPLIANCE

This is a national stage of PCT/DK05/000703 filed Nov. 3, 2005 and published in English.

The present invention relates to an ostomy appliance with a filter which may be cleaned during use, to an ostomy appliance comprising such a filter as well as to a method for cleaning of the filter.

BACKGROUND

The invention relates to ostomy appliances for receiving bodily waste from colostomy or ileostomy patients and in particular to the filters used in connection with ostomy bags for removal of malodour of flatus collected in the bag, before the gases are released to the environment.

A number of publications describes such filters and the problem with solid or semi-liquid waste blocking the filter and causing malfunctioning of the filter. Methods for protecting such filters from liquid and solid bodily waste are also described. Such methods include covering the inlet opening of the filter with a porous protection film and with a foam.

Thus, EP 607 028 discloses an ostomy bag for holding body waste comprising a bag formed from a flexible plastic sheet material defining a waste collection chamber. The bag defines a gas outlet proximate a top end portion of the bag. A deodorizing filter is joined to the bag in alignment with the gas outlet means for deodorizing gaseous waste material before the gaseous waste exits from the bag through the gas outlet. In the bag, there is provided means for protecting the deodorizing filter from contact with semi-liquid waste material, and for permitting the flow of gaseous waste, and for obstructing the flow of semi-liquid waste, the protection means comprises a porous protection film preceding the deodorizing filter and further comprising an open cell foam material preceding the porous protection film so that the gaseous waste has to pass through the open cell foam material, and thereafter through the porous protection film before it passes through the filter. It is thereby sought to provide a multi stage filter system that prevents semi-liquid waste material from contaminating the deodorizing element.

U.S. Pat. No. 6,135,976 discloses an ostomy appliance comprising a front wall and a rear wall of a flexible material. One of the walls has one or more vents through which gas may escape from the bag. The patent discloses a filter covering the vent, which filter comprises an elongated substantially flat filter body of a porous filter material interposed between gas and liquid permeable walls which are sealed to the filter body along its longitudinal edges. Gas inlet and outlet openings are provided in communication with the filter material in adjacent ends of the longitudinal filter. The gas and liquid impermeable walls are sealed to the upper and lower surfaces of the filter body. In use, gas flows longitudinally through the filter from the inlet opening to the outlet opening. The inlet opening is covered with a micro porous hydrophobic and oleophobic membrane, and a foam material is placed so that it precedes said membrane but also covers the inlet opening of the vent.

These filters have improved resistance to wetting and blocking of the deodorizing filter. However, even if improved, it has been found that such filters may eventually become blocked due to faeces being deposited therein, which is inconvenient and unpleasant for the patient.

The filters according to the present invention comprises a protective element in the form of an open celled compressible material having a memory and having a very small pore size, suitably the pore size is above 60 PPI (pores per inch).

It has been found that by the use of the protective element according to the invention, the membrane or the porous or perforated film covering the inlet opening of the deodorizing filters described above has become superfluous.

Moreover, it has been found that filters having protective elements extending in the direction of the gas flow and having a very small pore size may be cleaned in situ.

The filters described in the above publications generally describe the use of protective foam elements covered by foils allowing access of gases through a few small openings in the foil which prevents solid or semi-liquid bodily waste from entering the protective foam element. Thus, once bodily waste get into these protective foams and block for the passage of gases, they are difficult to clean due to the limited access to the protective foam elements.

The filters according to the invention are characterised by having a relatively large opening in the channel or compartment containing the protective element, the relatively large opening enabling in situ cleaning of the protective element by squeezing solid or semi-liquid waste out and away from the protective element.

None of the above-mentioned publications describes or suggest in situ cleaning of the filters for ostomy appliances.

SUMMARY

The present invention relates to a filter for an ostomy appliance comprising a pathway for leading gases to a vent in an ostomy bag and a protective element contained in said pathway to prevent solid or semi-liquid waste from blocking the pathway where a channel or compartment formed by liquid impermeable layer(s) is defining at least part of the pathway and at least a part of said compartment or channel contain a protective element of an open celled compressible material having a memory and having a pore size of at least 60 PPI, said protective element extending in the same direction as the gas flow within the channel or compartment, said channel or compartment having an opening providing access to the pathway from the interior of the bag, and said pathway having another opening being connected to a vent in the ostomy bag, optionally via a deodorizing filter.

In another embodiment, the invention relates to a filter for an ostomy appliance comprising a pathway for leading gases to a vent in an ostomy bag and containing a protective element in said pathway to prevent solid or semi-liquid waste from blocking said pathway where a channel or compartment formed by liquid impermeable layer(s) is defining at least part of the pathway and at least a part of said compartment or channel contain a protective element of an open celled compressible material having a memory, said protective element extending in the same direction as the gas flow within the channel or compartment, said channel or compartment having an opening providing access to the pathway from the interior of the bag and said pathway having another opening directly connected to the inlet opening of a deodorizing filter, so that gases which have passed the protective element are lead directly into the deodorizing filter.

In a final aspect, the invention relates to an ostomy appliance comprising a filter as above and a method for emptying or cleaning the filter.

DETAILED DISCLOSURE

FIG. 8b shows a sectional view of the filter of FIG. 8a.

Figure 1:
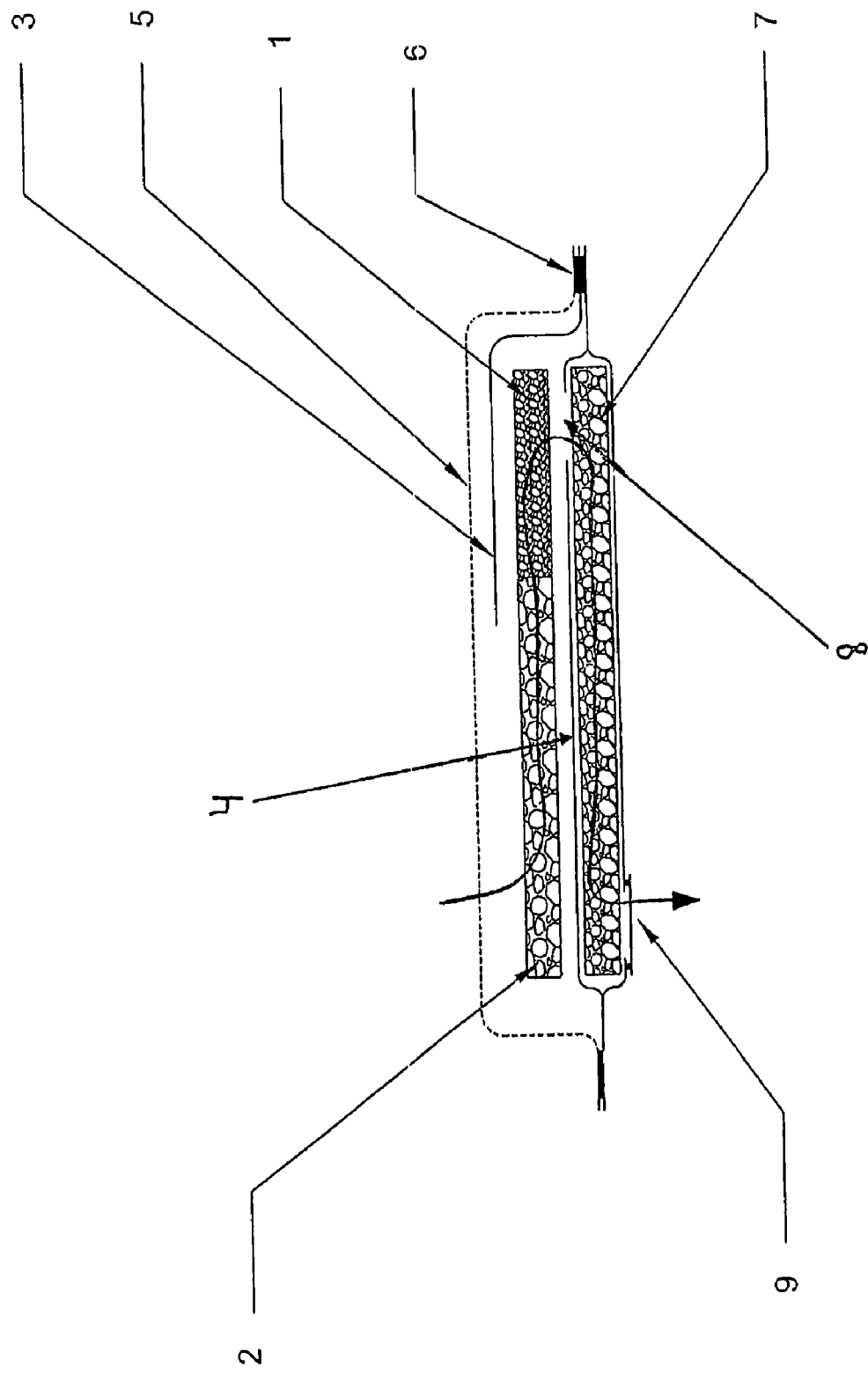
FIG. 1 shows a filter according to the invention having a flat, longitudinally extending shape and the same filter in combination with a deodorizing filter to form a layered structure.

During use of ostomy bags with filters protected by various foam elements or porous membranes, the filters may become blocked by solid or semi-liquid waste entering the foam material and/or coming into contact with a membrane placed to protect the gas inlet opening of the deodorizing filter. The known filters described above are designed to minimize access to the protecting elements within the pathway and thereby reduce the risk of these elements becoming blocked. The narrow passages, on the other hand, complicate the removal of waste material once it has entered into the protective element and is blocking the filter.

The present invention relates to a filter for an ostomy appliance which may be cleaned in situ during use.

According to the invention, filters which may be emptied and cleaned in situ are provided by creating a pathway for gaseous waste which is open in one end and connected to the gas inlet opening of the deodorizing filter body and/or a vent in an ostomy bag, in the other end. The pathway is filled with a protective element extending in the direction of the gas flow within the pathway. Suitably, the protective element is a foam, enclosed between liquid impermeable layers forming a channel or compartment defining at least part of said pathway. The compartment, channel and pathway have at least one opening in either end and may have many forms or shapes. Preferably, the compartment, channel and pathway have an opening in either end.

The pathway for gases is defined by gas impermeable, or gas and liquid impermeable layers.

The material used for the protective element according to the invention is an open celled compressible material with a memory having a particularly small pore size.

By open celled compressible material with a memory is meant a material having pores and/or cavities which are connected to each other allowing passage, at least of gases, and which may be compressed, suitably to the extend that the pores and cavities disappear, but the material essentially resumes its original structure with pores and/or cavities once the pressure is removed from the material (the material has a memory).

Such open celled compressible material with a memory may be selected from various foam materials, woven and non-woven material of fibres, such as polymer fibres, or metal fibres, a material consisting of numerous elastic bodies, suitable having spherical shape, of a material which may be compressed and has a memory.

According to a preferred embodiment of the invention, the open celled compressible material with a memory is a foam. Suitable foams may be selected from polystyrene, polyvinylchloride, polyethylene, polyurethane, polyphenol, polyester and silicone or polyisocyanate foam, such as polyester- or polyether based polyurethane foam.

The use of a material having a low pore size within the pathway provides an effective stopper ensuring the blockade of the pathway does not become permanent.

According to a preferred embodiment of the invention, the material used for the protective element is a material having a pore size of at least 80 PPI, suitably a pore size between 60 and 200 PPI, more preferred a pore size between 60 and 150 PPI and most preferred a pore size between 80 and 100 PPI.

PPI means pores per inch and is measured by counting the number of walls between pores, which is passed per inch, when passing linearly over a surface of the material.

The protective element having the small pore size may have a uniform pore size throughout the element. Alternatively, the protective element has a gradually decreasing pore size going from one end of the element to the other end of the element within the pathway, the pore size decreasing in the same direction as the intended direction for the gases to be passing through the pathway.

The protective element may be preceded in the pathway by additional protective element(s), in particular protective elements having a larger pore size. The additional protective element(s) are suitably placed in continuation of, and in direct contact with the protective element with the small pore size, so that the gases and other waste material passes the element with the largest pore size before it passes the protective element with the small pore size.

The additional protective element(s) also consist of an open celled compressible material having a memory and have a PPI below 60.

Suitable, the additional protective elements having the larger pore size has a pore size between 20 and 60 PPI (pores per inch), suitably PPI is around 40.

Each additional protective element may have a uniform pore size or it has a gradually decreasing pore size going from the one end of the additional protective element(s) to the other end, the pore size decreasing in the same direction as the direction of the gas flow.

According to one embodiment of the invention, the protective element and the additional protective element(s) are made form one single piece of open celled compressible material, for example a material having a gradually decreasing pore size, where the part having a pore size above 80 is the protective element having the small pore size and the part having a PPI below 80 being the "additional protective element". In another embodiment, the protective element consist of two or more pieces of an open celled compressible material with a memory, being placed in continuation of each other and pressed, welded, glued or in any other way held together within the pathway.

A protective element with a gradually decreasing pore size may be achieved by squeezing the protective element within the pathway, for example by using the same volume of protective element in the whole length of the channel or compartment, but constructing the channel or compartment containing the protective element so that it becomes narrower in the direction of the gas flow. Alternatively, a larger volume of protective element is used in one end of the channel or compartment compared to the other end.

An alternative way of achieving material with different pore sizes would be to coat or fill the protective element or a part of a protective element with a material reducing the pore size, or alternatively enlarging or creating holes in a material or a part of a material. According to these embodiment(s) of the invention, the protective element and any additional protective element(s) may be in the form of one single unit which have been treated to obtain an element with a pore size above 80 PPI in one end and a pore size below 80 PPI in the other end.

The protective element and the additional protective element(s) need not be made from the same type of material. Thus, one of the elements may be a foam and the other element may be a fiber material. Suitably however, both types of protective elements are of a foam material.

The term "shortest pathway" within the channel or compartment means the shortest pathway through the part of the channel or compartment which is filled with the protective element, in a "hypothetical" situation where the protective element is not present in the compartment or channel.

According to the invention, the part of the channel or compartment, which is filled with the protective element, defines a shortest pathway which extends longitudinally within the channel or compartment in the same direction as the gas flow. Preferably, the protective element extends longitudinally within a channel.

The dimensions of the protective element and thereby also the channel or compartment formed by the liquid impermeable layers is suitably such that the shortest pathway through the protective element is as least as long, preferably more than 50% longer, or most preferred more than 100% longer than the most narrow cross-section perpendicular to the shortest pathway defined above.

It is important that the protective element and additional protective element(s) fits tightly with the walls of the channel or compartment in order to prevent solid or semi-liquid waste from bypassing the protective elements. This may be achieved by the use of a protective element(s) with a volume which fit into the channel or compartment formed by the liquid impermeable layers, or is a little larger. The protective element(s) may be attached to the liquid impermeable layers forming the channel or compartment by gluing, lamination, welding or by any other suitable methods.

Faeces blocking the foam element may be removed from the foam element by providing a pressure, for example a manual pressure using the fingers, on the part of the gaseous pathway defined by the liquid impervious layers and containing the protective element(s) and squeezing or pushing the solid or semi-liquid waste blocking the protective element out and away from the gaseous pathway formed by the liquid impermeable layers, suitably, but not necessarily in the direction opposite the direction of the gas flow. Once faeces have been removed from the protective element(s), the protective element(s) essentially, or at least partly, resumes its original volume and pore structure allowing gases to pass through the protective element. According to the invention, the ostomy patient may clean the filter easily and as often as necessary.

By "in situ cleaning" is meant that the filter can be cleaned without removing any parts or elements of the filter from its location. The cleaning is typically done by simply adding pressure to relevant filter parts or elements, e.g. the protective element.

In one embodiment of the invention the protective element may be displaced in relation to the deodorizing element so that the area which the user has to press in order to clean the filter is correspondingly displaced. This displacement provides the advantage of being able to place the area, which the user has to press in order to clean the filter, in a position which is particularly advantageous, e.g. for accommodating ease of use and/or accessibility for the user. The relative placement of the protective element and the deodorizing element can be done in numerous ways which will be appreciated by the skilled person.

It is important that the opening in the channel or compartment accommodating the protective element is sufficiently large to allow particle and semi-liquids which have entered the element to be removed from the protective element by squeezing the element in the direction of the opening providing access to the pathway from the interior of the ostomy bag.

In order to achieve efficient removal of material blocking the protective element(s), the area of the opening in the channel or compartment providing access to pathway from the interior of the ostomy bag preferably corresponds to the cross-sectional area of the protective element, in its essentially uncompressed form, in the end closest to said opening in the channel or compartment.

In one particular embodiment of the invention a part of the protective element and/or additional protective element(s) is sticking out of said opening providing access to the pathway from the interior of the ostomy bag.

According to one embodiment of the invention at least the opening providing access to the pathway from the interior of the ostomy bag is covered by a perforated foil.

The perforated foil or a woven or non-woven material, suitably based on polyethylene, polyvinylchloride, polypropylene, PVDC, EVA (ethylene-vinyl acetate), polyester or other polymeric materials.

The pore size in the perforated foil may be between 3 μm and 2 mm, suitably between 10 μm and 500 μm in diameter.

Due to the numerous pores in the perforated foil or the non-woven material, solid or semi-liquid waste which have crossed the barrier represented by the perforated foil or non-woven material and entered the protective element(s), may easily be removed.

The liquid impermeable layers and the gas and liquid impermeable layers used according to the invention are suitably made from foils of polyethylene, EVA or other suitable polymeric materials.

The liquid impermeable layers and the gas and liquid impermeable layers are suitably of a kind that may be welded together.

Various ways of constructing a filter according to the invention may be considered.

According to one particular embodiment of the invention, the protective element(s) consists of two oblong pieces of foam having different pore size, being placed in continuation of each other. According to this embodiment of the invention, the foam element is an essentially flat foam layer wherein the two pieces of foam taken together are at least double as long as they are broad and at least as broad as they are thick. Typically, the dimensions of the oblong foam elements having two zones with different pore size is 10-80 mm long, 3-20 mm broad and 1-5 mm thick. Preferably, the dimensions of the oblong foam elements having two zones with different pore size are 3 mm×8 mm×40 mm.

According to this embodiment of the invention, the oblong pieces of foam are contained in a channel formed by liquid impermeable layers having an opening in either end of the channel. The opening in the end of the channel closest to the foam element with the smallest pore size may at the same time be the inlet opening to a deodorizing filter or a vent. The deodorizing filter may be placed in continuation of the protective foam elements or it may be placed as a layer below or above the foam element. These different embodiments are illustrated in FIG. 1.

According to this embodiment, the protective element(s) between liquid impermeable layers and the deodorizing filter consist of an essentially flat structure, however, the protective element(s) and/or the deodorizing filter could also have the form of a rod in a channel formed by liquid impermeable layers.

Figure 4:
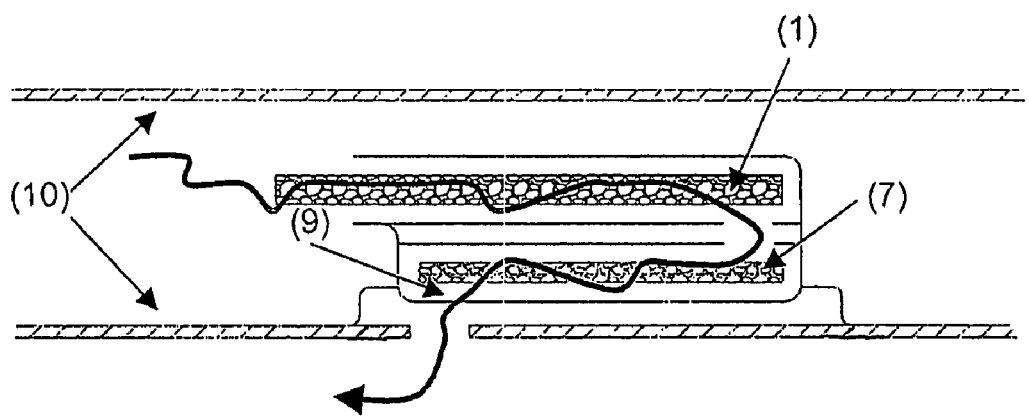
FIG. 4 shows a very simple, low cost filter according to the invention and the combination thereof with a deodorizing filter to form a layered structure.

According to another more simple embodiment of the invention, the foam element consists of a single oblong foam element having a small pore size, suitably above 60 PPI, which is at least as long as it is broad, and as least as broad as it is high. The foam element is laminated between two liquid impermeable layers, creating a channel having an opening in both ends. The channel may be laminated or welded on top of a deodorizing filter or placed in continuation of a deodorizing filter. This embodiment of the invention is illustrated in FIG. 4.

Of course each oblong protective element need not be a foam element but may be a protective element made from any other open celled compressible material with a memory having the appropriate pore size.

Figure 2:
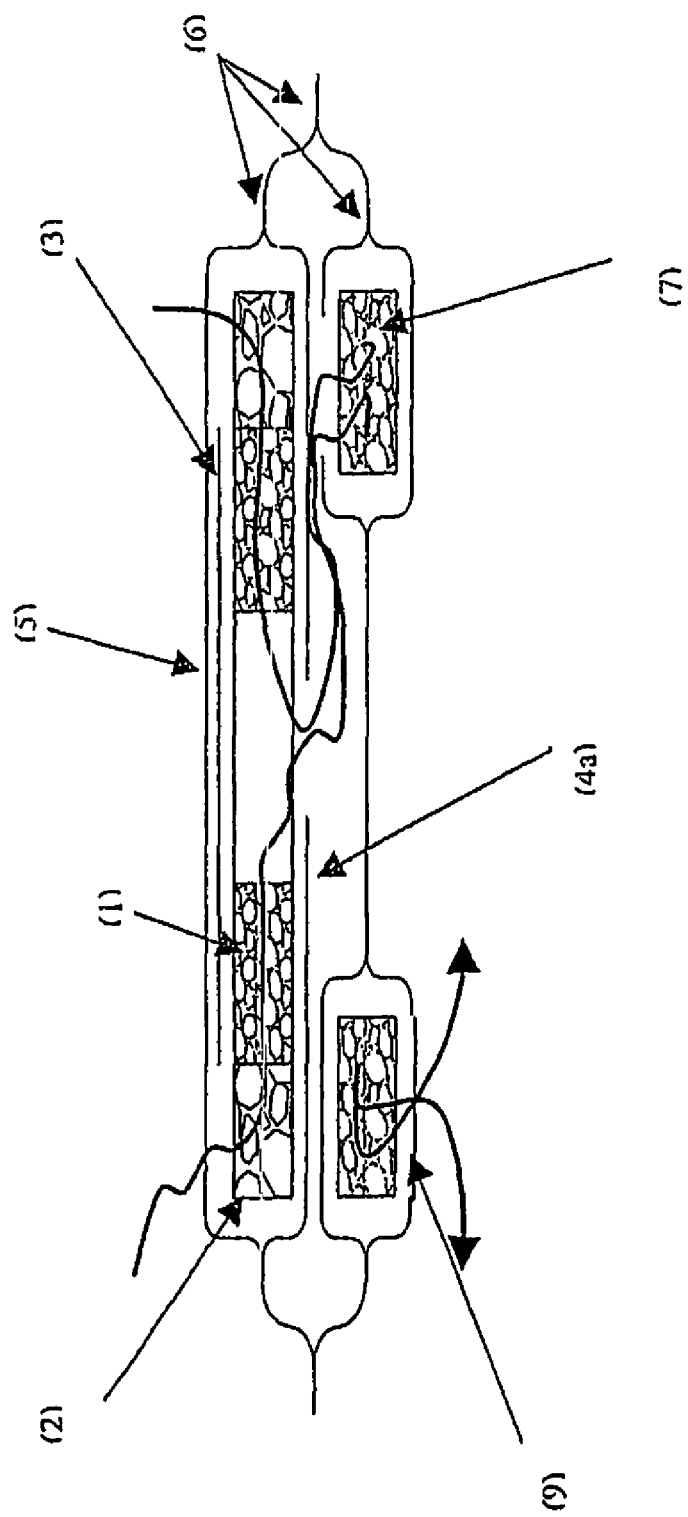
FIG. 2 shows a sectional view of a filter according to the invention having a flat, essentially circular or ring formed shape and the combination thereof with a deodorizing filter to form a layered structure.

According to another embodiment of the invention, the protective element(s) have the form of two or more essentially flat, concentric rings of protective material having the protective element with the smallest pore size placed closest to the hole in the centre of the circle formed by the rings. According to this embodiment, the circular protective element(s) with or without a hole in the middle have at least a part of the one of its surfaces covered by a liquid impermeable layer, suitable a circular liquid impermeable layer, and the opposite surface of the protective element is covered with a liquid impermeable layer having essentially the same shape and having a hole. These liquid impermeable layers form a compartment in which gases are lead between the to liquid impermeable layers, through the concentric rings of protective element(s) and through the hole in the liquid impermeable layer and thereafter to a deodorizing filter or a vent in the ostomy bag. FIG. 2 illustrates this embodiment of the invention having a deodorizing filter with a flat ring formed structure welded to the pathway containing the protective element(s), thereby forming a flat compact structure.

The flat structure according to this embodiment of the invention, where gases are lead to a hole in the middle of an flat protective element, need not have a circular shape but could have any other convenient shape, such as ellipsoid, rectangular, etc.

The form and shape of the pathway leading the gases from the hole in the middle of the flat structure to the deodorizing filter or vent is not particularly important as long as it defines a pathway for the gases. FIG. 2 shows one way of creating a pathway for the gases to a deodorizing filter.

The deodorizing filter used according to the present invention may be any suitable deodorizing filter known in the art. Suitable the deodorizing agent is active carbon impregnated onto an open cell foam. These active filters are suitably formed as oblong flat elements being 20-60 mm long, 5-10 mm broad and 2-5 mm high, or as circular discs having a diameter of 20-40 mm and being 2-5 mm thick. In one embodiment, the deodorizing filer has an elongated structure fitting the contours of the upper portion of the ostomy bag.

According to one embodiment of the invention, the pathway with the protective element(s) enclosed within liquid impermeable layer(s) and the deodorizing filter form a layered structure comprising the deodorizing filter in the form of one layer and the protective element(s) enclosed within liquid impermeable layer(s) as a second layer and optionally a perforated foil as a third layer, all of the layers, optionally being sealed to each other along the periphery of the layers. According to this embodiment of the invention, all layers suitably have the same area and shape.

The invention also relates to an ostomy appliance comprising a filter as described above.

In order to prevent ballooning during cleaning of the filters of the invention, the filters should be placed close to an edge of the ostomy appliance, preferably welded to an edge and/or the walls of the ostomy bag, suitably in the upper part of the ostomy bag.

According to this embodiment of the invention, the filter is positioned within the ostomy bag and is welded to the peripheral edge of the bag and/or the wall(s) of the bag, suitable in the upper part of the bag.

Suitably, the filter is welded to both walls of the ostomy bag, or placed or welded into a pocket or channel formed by welding both walls of the ostomy bag to each other in a position close to the edge of the ostomy bag.

Figure 9:
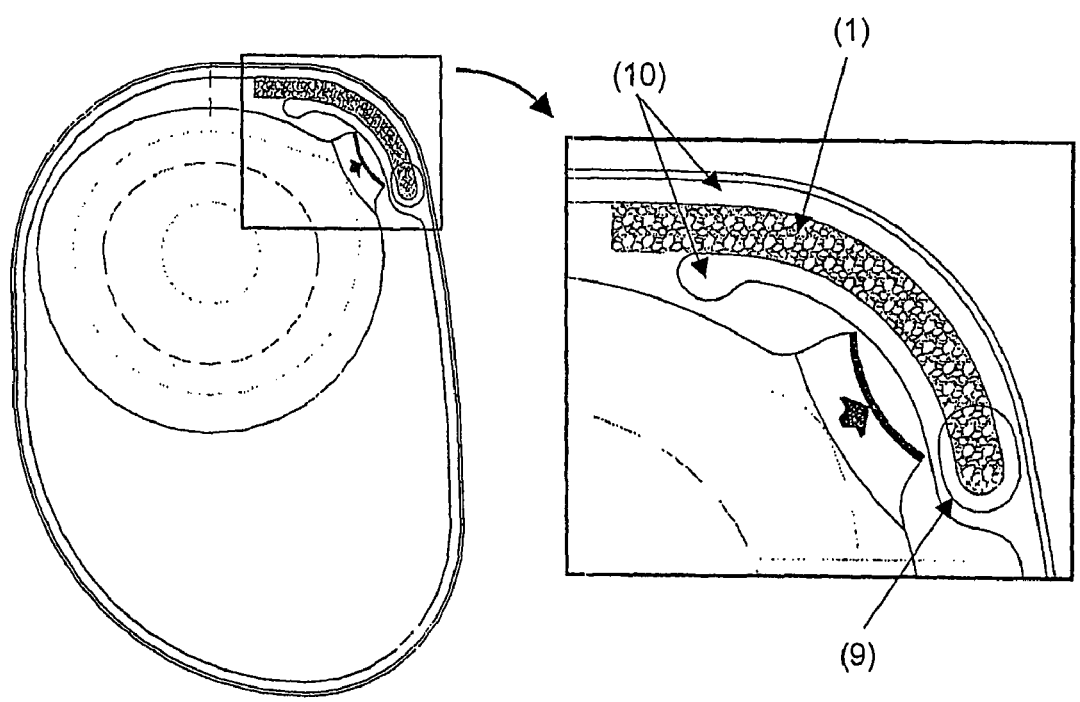
FIG. 9 shows the position of a filter of the invention within an ostomy bag.

Alternatively, the filter may be placed in a pocket created at the edge of the ostomy bag. FIG. 9 illustrates this embodiment of the invention.

According to the invention, the gas outlet or vent of the ostomy bag may be covered by a perforated film or membrane.

FIGURES

FIG. 1 shows an essentially flat, oblong filter according to a preferred embodiment of the invention. The filter comprises two oblong pieces of foam (1,2) placed in continuation of each other. The foam element (1) has a small pore size, and the foam element (2) has a large pore size. The foams are placed in a channel formed by the two liquid impermeable layers (3,4), and the liquid and gas impermeable layer (4) has a gas inlet opening (8) into the porous material (7) containing a deodorizing agent (e.g. active carbon). The welding of the liquid impermeable layers is made so that the foils (3,4) fit closely to the two pieces of foam, allowing no by-pass of liquid waste in the channel. Preferably, the foam element is glued or welded to the side walls of the channel formed by the liquid impermeable layers (3,4). A part of the foam element having the largest pore size (2) is extending out of the channel. In this figure, the foam and the liquid impermeable layer (3) is covered by a perforated foil (5) which is sealed (6) to the gas and liquid impermeable layers. In this figure, the outlet opening (9) is covered by a membrane, e.g. a perforated foil.

FIG. 2 shows an alternative embodiment of the invention wherein the filter is a circular essentially flat construction. The filter comprises two concentric foam layers with different pore size (1,2) fitted into a channel formed by liquid impermeable layers (3, 4a) creating a pathway for gases which goes through foam element (2) having a large pore size and thereafter through foam element (1) having a small pore size and via the hole in the middle of the foam element to the gas inlet opening of a deodorizing filter welded (6) on top of the deodorizing filter, which is also circular and has the same centre as the foam layer. The perforated layer (5) is sealed to a liquid impermeable layer layers (4a), suitably by welding along the periphery. In this figure the outlet opening (9) is covered by a membrane, e.g. a perforated foil.

Figure 3B:
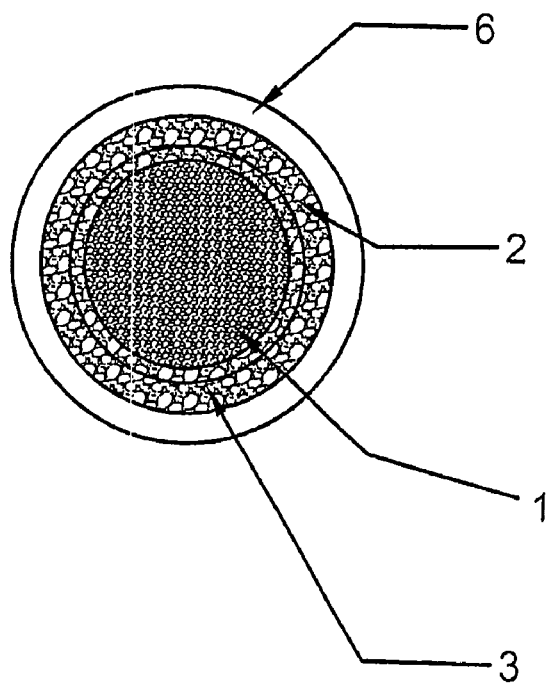
FIG. 3b shows a top view of the filter of FIG. 2.
Figure 3A:
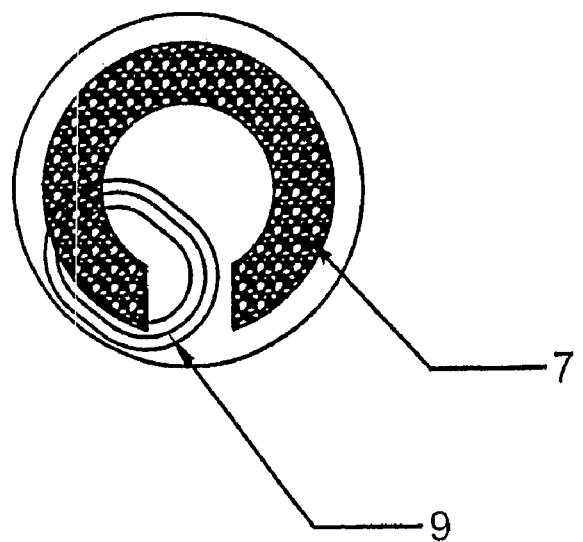
FIG. 3a shows a bottom view of the filter of FIG. 2.

FIG. 3a shows a bottom view of the filter of FIG. 2 showing the position of the deodorizing element (7) and the outlet opening (9).

FIG. 3b shows a top view of the filter of FIG. 2 showing the position of the two concentric foam layers with different pore size (1,2), the liquid impermeable layer (3), and a welded (6) area.

FIG. 4 shows yet another embodiment of the invention where an oblong foam element (1) having a small pore size which is preferably at least twice as long as it is broad and is at least as broad as it is high. The foam element is placed or laminated between two liquid impermeable foils forming a channel with an opening in both ends, one end having connection to the interior of e.g. an ostomy bag and the other end being in connected to the filter body via the inlet opening of the deodorizing filter (7). The channel fits tightly around the foam. In this figure the outlet opening (9) is covered by a membrane, e.g. a perforated foil. The filter is welded to a wall (10) of the ostomy bag.

Figure 5:
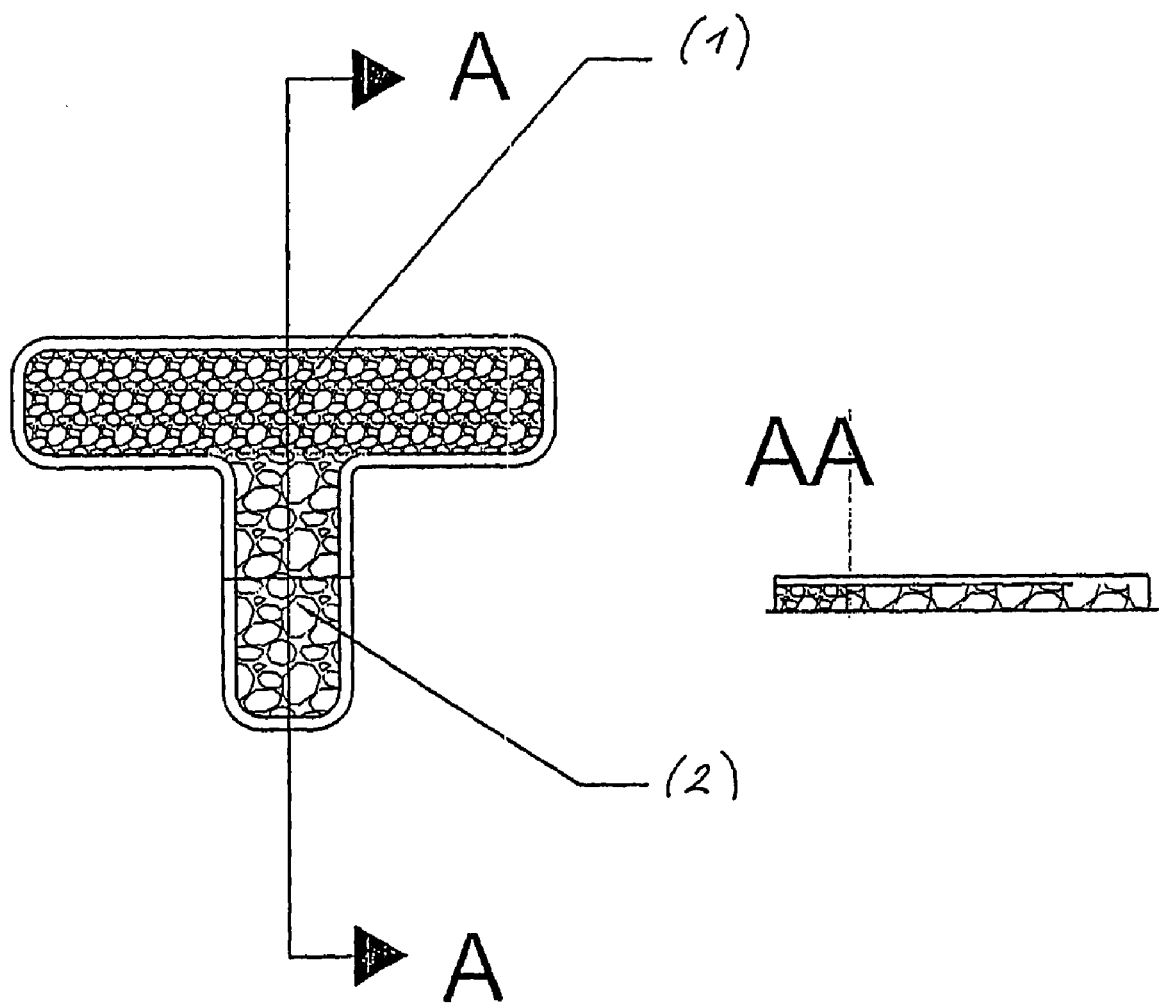
FIGS. 5, 6 and 7 show various embodiments of a filter according to the invention.
Figure 6:
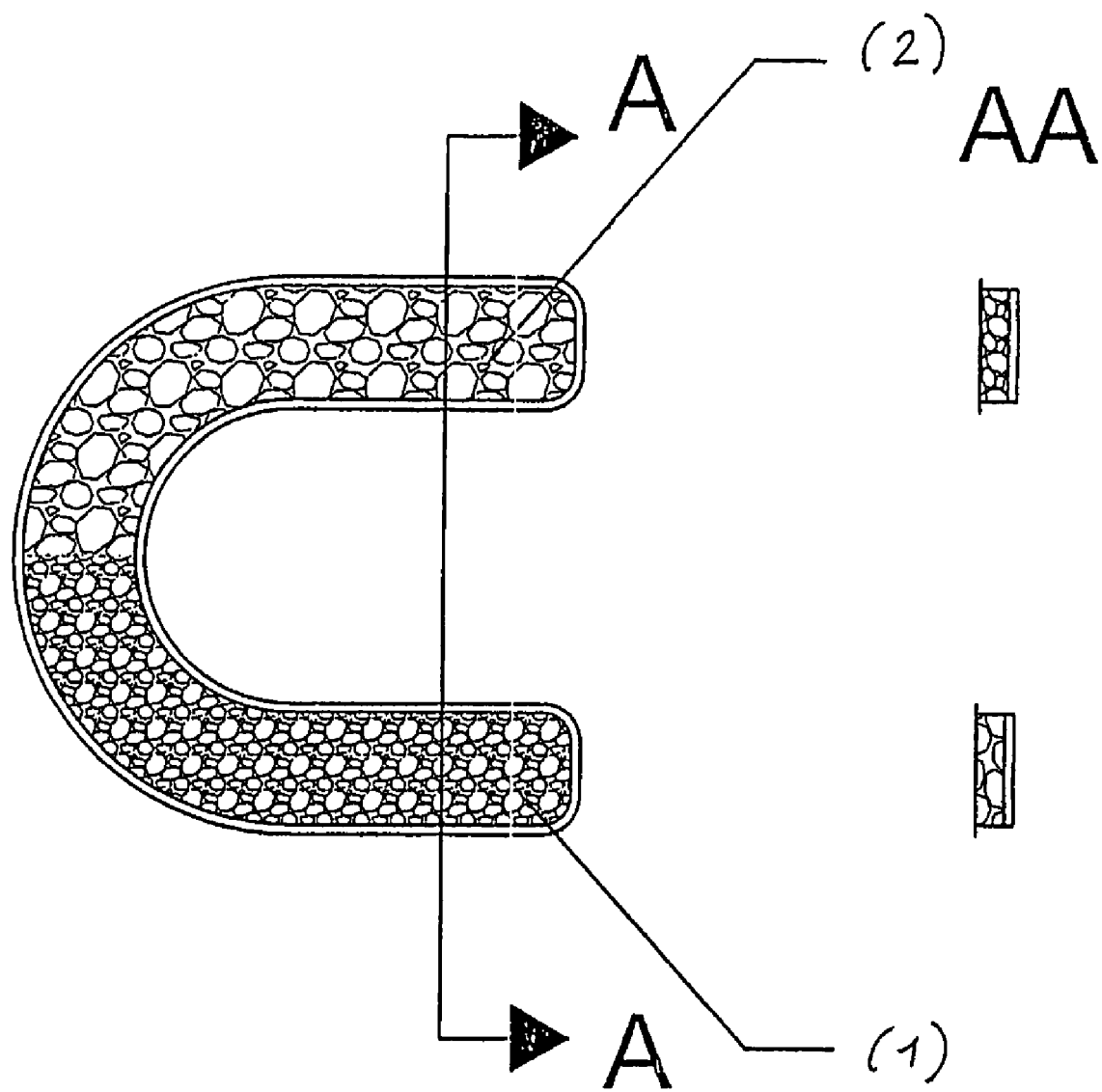
Figure 7:
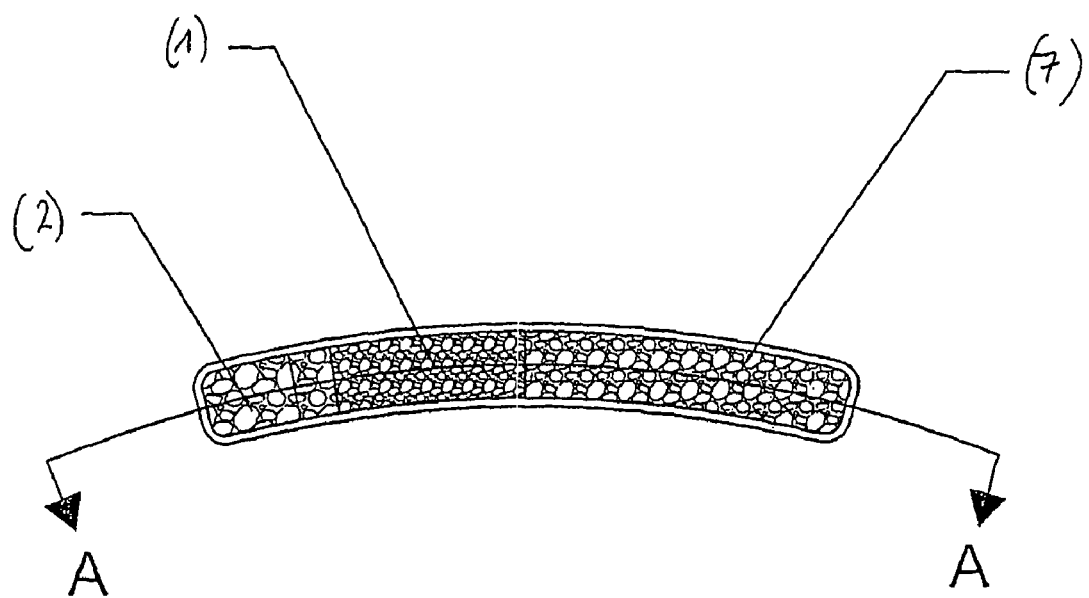
Figure 7:

FIGS. 5, 6 and 7 show other filters according to the invention, showing the position of foam having a small pore size (1), foam having a large pore size (2) and a deodorizing element (7).

Figure 8A:
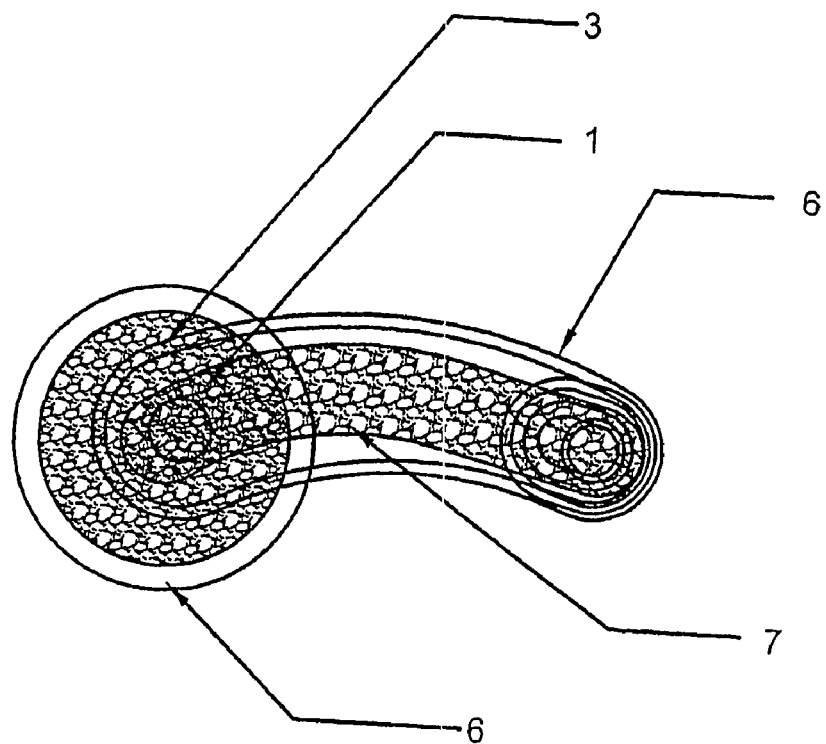
FIG. 8a shows a top view of another embodiment of a filter according to the invention.
Figure 8B:
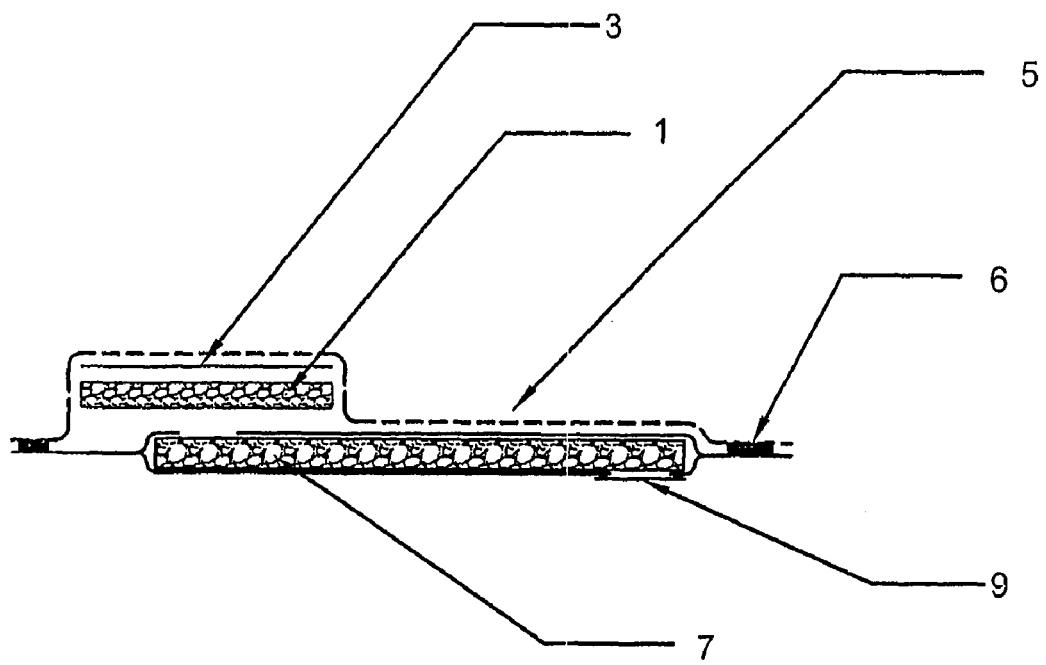

FIGS. 8a and 8b show an embodiment of the invention where the foam element (1) is displaced in relation to the deodorizing element (7) so that the foam element (1) is placed relatively closer to one end of the oblong deodorizing element (7) than the other.

FIG. 9 shows the position of the filter according to the invention at an upper edge in an ostomy bag. In the figure an oblong and curved filter (1) according to the invention has been welded into a pocket formed by welding (10) the filter to both walls of the ostomy bag and to the edge of the ostomy bag (10). In this figure, the outlet opening (9) is covered by a membrane, e.g. a perforated foil.

The invention claimed is:

1. A filter for an ostomy appliance comprising a pathway for leading gases to a vent in an ostomy bag and a protective element in said pathway to prevent solid or semi-liquid waste from blocking the pathway, a channel or compartment formed by liquid impermeable layer(s) defines at least part of the pathway and at least a part of said compartment or channel contain said protective element, said protective element extending in the same direction as gas flow within the channel or compartment, said channel or compartment having a first opening providing access to the pathway from an interior of the bag, and said pathway having a second opening being connected to a vent in the ostomy bag, and characterized in that the protective element is of an open celled compressible material having a memory and wherein said protective element has a decreasing pore size from one end of said protective element to an other end of said protective element.

2. The filter according to claim 1 wherein the part of the channel or compartment is filled with the protective element and defines a shortest pathway that extends longitudinally within the channel or compartment in the same direction as the gas flow.

3. The filter according to claim 1 wherein the pathway has an opening directly connected to an inlet opening of a deodorizing filter, so that gases that have passed the protective element are lead directly into the deodorizing filter.

4. The filter according to claim 2 wherein the shortest pathway is more than 100% longer than a most narrow cross-section of the protective element perpendicular to said shortest pathway.

5. The filter according to claim 1 wherein the protective element is extending longitudinally within a channel formed by liquid impermeable layers.

6. The filter according to claim 1 wherein the protective element has a uniform pore size throughout the protective element.

7. The filter according to claim 1 wherein the pore size decreases in a direction from the first opening toward the second opening.

8. The filter according to claim 1 wherein said protective element is preceded in said pathway by one or more additional protective element(s) of an open celled compressible material having a memory and having a PPI below 60.

9. The filter according to claim 8 wherein the additional protective element(s) has a uniform pore size.

10. The filter according to claim 8 wherein the additional protective element(s) has a gradually decreasing pore size, the pore size decreasing in a direction from the first opening toward the second opening.

11. The filter according to claim 8 wherein the protective element and the additional protective element(s) lie in continuation and in contact with each other or the protective element and the additional protective element(s) form a single unit.

12. The filter according to claim 1 wherein an area of the first opening in said channel or compartment providing access to the pathway from the interior of the ostomy bag corresponds to a cross-sectional area of the protective element in an end closest to said first opening in the channel or compartment.

13. The filter according to claim 1 wherein at least the first opening providing access to the pathway from the interior of the ostomy bag is covered by a perforated foil or a non-woven material.

14. The filter according to claim 1 wherein the protective element is a foam selected from one of polyester- or a polyether based polyurethane.

15. The filter according to claim 3 wherein the filter has a layered structure comprising a deodorizing filter in the form of one layer, the protective element enclosed within liquid impermeable layer(s) as a second layer on top of the deodorizing filter and a perforated foil as a third layer, the layers sealed to each other along a periphery of the layers.

16. The filter according to claim 3 wherein the protective element(s) enclosed within liquid impermeable layer(s) and a deodorizing filter is placed in continuation of each other in an longitudinally extending structure.

17. An ostomy appliance comprising a filter according to claim 1 connected to the vent of the ostomy bag.

18. The ostomy appliance according to claim 17 wherein the filter is positioned within the ostomy bag and is welded to a peripheral edge of the bag and/or the wall(s) of the bag.

19. The ostomy appliance according to claim 18 wherein the filter is welded to both walls of the ostomy bag.

20. A method for cleaning a filter according to claim 1 comprising providing a pressure on the pathway defined by the liquid impermeable layers containing the protective element(s) and squeezing or pushing solid or semi-liquid waste contained in the protective element(s) or in the vicinity of the protective element(s) out and away from the channel or compartment containing the protective element.

21. The filter according to claim 1 wherein the gases are adapted to flow in a first direction to the vent in the ostomy bag and said decreasing pore size decreases in the first direction.

22. The filter according to claim 1 wherein said protective element has a pore size above 80 PPI at the one end of said protective element and a pore size of below 80 PPI at the other end of said protective element.

23. The filter according to claim 1 wherein said protective element has a pore size of at least 60 PPI.

* * * * *